United States Patent
Forcucci et al.

(10) Patent No.: US 10,463,477 B2
(45) Date of Patent: Nov. 5, 2019

(54) RETRIEVABLE DEVICES FOR TREATING HEART FAILURE

(71) Applicant: Corvia Medical, Inc., Tewksbury, MA (US)

(72) Inventors: Stephen J. Forcucci, Winchester, MA (US); Matthew J. Finch, Medford, MA (US)

(73) Assignee: Corvia Medical, Inc., Tewksbury, MA (US)

( * ) Notice: Subject to any disclaimer, the term of this patent is extended or adjusted under 35 U.S.C. 154(b) by 323 days.

(21) Appl. No.: 15/346,711

(22) Filed: Nov. 8, 2016

(65) Prior Publication Data
US 2017/0128705 A1    May 11, 2017

Related U.S. Application Data

(60) Provisional application No. 62/253,124, filed on Nov. 9, 2015.

(51) Int. Cl.
| | | |
|---|---|---|
| *A61F 2/24* | (2006.01) | |
| *A61F 2/90* | (2013.01) | |
| *A61F 2/966* | (2013.01) | |
| *A61F 2/95* | (2013.01) | |

(52) U.S. Cl.
CPC .............. *A61F 2/24* (2013.01); *A61F 2/90* (2013.01); *A61F 2/2418* (2013.01); *A61F 2/966* (2013.01); *A61F 2002/9528* (2013.01); *A61F 2230/0067* (2013.01); *A61F 2250/0039* (2013.01)

(58) Field of Classification Search
CPC .. A61F 2/90; A61F 2/24; A61F 2/2415; A61F 2/2418; A61F 2/996; A61F 2002/9528; A61F 2230/0067; A61F 2250/0039; A61F 2/2427
See application file for complete search history.

(56) References Cited

U.S. PATENT DOCUMENTS

| | | | | |
|---|---|---|---|---|
| 2012/0165928 A1* | 6/2012 | Nitzan | ................... | A61F 2/2415 623/2.15 |
| 2014/0012368 A1* | 1/2014 | Sugimoto | ............. | A61L 31/022 623/2.11 |

* cited by examiner

*Primary Examiner* — Philip R Wiest
(74) *Attorney, Agent, or Firm* — Helen S Liu

(57) ABSTRACT

The present teachings provide devices to change the pressure in a chamber of a heart and methods of making and using thereof. One aspect of the present teachings provides a device comprising a distal portion, a middle portion, and a proximal portion. The distal portion and proximal portion of the device are configured to be deployed inside the left and right atrium respectively with a minimum contact with the septal tissue. The middle portion of the device is configured to secure the device across an aperture on the atrial septum. The device further includes at least one retrieval portion with a plurality of struts. The distal end of the struts is connected with a proximal end of the proximal portions. The proximal end of the struts come together at a location near the axial center of the device. The radial expansion of the proximal portion will lead to the radially outward movement of the struts. And a radially inward movement of the struts will cause the proximal portion of the device to collapse radially. The device includes a delivery profile and a deployment profile.

9 Claims, 5 Drawing Sheets

RETRIEVABLE DEVICES FOR TREATING HEART FAILURE

CROSS-REFERENCE TO RELATED APPLICATION

The present application claims priority to and the benefit of U.S. Provisional Application Ser. No. 62/253,124, filed on Nov. 9, 2015, which is incorporated herein by reference in its entirety.

FIELD

The present teachings relate to devices and methods of use thereof for treating heart failures. An aspect of the present teachings relates to a device that can be used to change (e.g., reduce) the blood pressure in a heart chamber, for example, by creating a shunt, and optionally regulate the flow of blood through the shunt in order to enhance the therapeutic effect of the shunt. The present teachings further relate to a method of utilizing such a device, for example, in treating congestive heart failure and the related conditions, for example, acute cardiogenic pulmonary edema caused by an elevated pressure in a left side chamber in the heart.

BACKGROUND

Congestive heart failure (CHF) is a condition that affects millions of people worldwide. CHF results from a weakening or stiffening of the heart muscle that commonly is caused by myocardial ischemia (due to, e.g., myocardial infarction) or cardiomyopathy (e.g., myocarditis, amyloidosis). CHF causes a reduced cardiac output and inadequate blood to meet the needs of body tissues.

Treatments for CHF include: (1) pharmacological treatments, (2) assisting systems, and (3) surgical treatments. Pharmacological treatments, e.g., with diuretics, are used to reduce the workload of a heart by reducing blood volume and preload. While pharmacological treatments can improve quality of life, they have little effect on survival. Assisting devices, e.g., mechanical pumps, are used to reduce the load on a heart by performing all or part of the pumping function normally done by the heart. However, in a chronic ischemic heart, high-rate pacing may lead to an increased diastolic pressure, calcium overload, and damages to the muscle fibers. There are at least three surgical procedures for treating a heart failure: (1) heart transplant, (2) dynamic cardiomyoplasty, and (3) the Batista partial left ventriculectomy. These surgical treatments are invasive and have many limitations.

CHF is generally classified into systolic heart failures (SHF) or diastolic heart failures (DHF). In a SHF, the pumping action of a heart is reduced or weakened. A normal ejection fraction (EF), the volume of blood ejected out of the left ventricle (stroke volume) divided by the maximum volume remaining in the left ventricle at the end of the diastole or relaxation phase, is greater than 50%. In a systolic heart failure, EF is decreased to less than 50%. A patient with SHF may have an enlarged left ventricle because of cardiac remodeling developed to maintain an adequate stroke-volume. This pathophysiological phenomenon is often associated with an increased atrial pressure and an increased left ventricular filling pressure.

DHF is a heart failure without any major valve disease even though the systolic function of the left ventricle is preserved. Generally, DHF is a failure of the ventricle to adequately relax and expand, resulting in a decrease in the stroke volume of the heart. Presently, there are very few treatment options for patients suffering from DHF. DHF afflicts between 30% and 70% of patients with CHF.

There are several techniques that can be used to treat the symptoms of DHF. Without attempting to characterize the following references, for example, U.S. Pat. No. 8,091,556 by Keren et al. discloses the use of an interatrial pressure relief shunt with a valve and a tissue affixation element at each end of the shunt; and United States Patent Application Publication No. 20050165344 by Dobak discloses a pressure relief system with an interatrial septal conduit with an emboli barrier or trap mechanism to prevent cryptogenic stroke due to thrombi or emboli crossing the conduit into the left sided circulation. Dobak also discloses a conduit with a one-way valve which directs blood flow from the left atrium to the right atrium.

The constantly evolving nature of heart failures represents a significant challenge for the treatment. Therefore, there is a need for novel and adaptable methods and devices for treating DHF, for example, by creating a pressure relief shunt which can be retrieved, repositioned, adjusted, expanded, contracted, occluded, sealed and/or otherwise altered as required to treat a patient. Furthermore, there exists a need for treating DHF with devices and methods that can self-adjust over time either in accordance with or in anticipation of the gradual hemodynamic changes associated with a heart failure.

SUMMARY

An aspect of the present teachings provides devices for regulating the blood pressure in a heart chamber. In various embodiments, each of the devices comprises a shunt positionable across a septum of a heart, including, in the fossa ovalis. In various embodiments, the device is of a unitary construction. In some embodiments, the device is configured to be positioned across an aperture in an atrial septum. The device has a first elongated configuration, and a second radially expanded deployed configuration.

In various embodiments, the device comprises a distal portion with a first elongated configuration and a second radially expanded configuration. In the second radially expanded configuration, the distal end of the distal portion has a size greater than the proximal end of the distal portion.

In various embodiments, the device further comprises a proximal portion with a first elongated configuration and a second radially expanded configuration. In the second radially expanded configuration, the proximal end of the proximal portion has a size greater than the distal end of the proximal portion.

In various embodiments, the device further comprises a middle portion joining the distal end of the proximal portion at one end, and the proximal end of the distal portion at the other end.

In various embodiments, the device further comprises a retrieval portion joining the proximal end of the proximal portion. According to some embodiments, the retrieval portion comprises a plurality of struts. The retrieval portion also has a first elongated configuration wherein the plurality of struts are straightened and kept close to one another, and proximal to the elongated proximal portion; and a second radially expanded configuration wherein one end of at least one of the plurality of struts is positioned radially outwardly from the other end of the strut.

In various embodiments, in its second radially expanded configuration, the device further comprises an opening configured to allow blood to flow from a first end through the device to a second end. In various embodiments, in its second radially expanded configuration, at least one of the expanded distal and proximal portions of the device is configured to have a minimum contact with the surrounding septal tissues. In various embodiments, in its second radially expanded configuration, the expanded proximal portion of the device is larger than the distal portion of the device. In various embodiments, in its second radially expanded configuration, the expanded retrieval portion is proximal to the expanded proximal portion of the device. In various embodiments, in its second radially expanded configuration, the expanded retrieval portion is within a general structural space of the expanded proximal portion. In various embodiments, the device further comprises a proximal hub configured to attach to a percutaneous delivery system.

In various embodiments, the device comprises two retrieval portions, the first retrieval portion joining the proximal end of the proximal portion, and the second retrieval portion joining the distal end of the distal portion. Both the first and second retrieval portions comprise a plurality of struts. Both the first and second retrieval portions comprise a first elongated configuration wherein the plurality of struts are straightened and kept close to one another, and a second radially expanded configuration wherein one end of at least one of the plurality of struts is positioned radially outwardly from the other end of the strut. In various embodiments, in the second radially expanded configuration, the second retrieval portion is within a general structural space of the expanded distal portion.

In various embodiments, the device comprises a plurality of lengthwise supports joining with a plurality of perimeter supports. In some embodiments, at least one perimeter support joins a distal end of the plurality of lengthwise supports. In some embodiments, at least one perimeter support joins with a proximal end of the plurality of lengthwise supports. In some embodiments, at least one perimeter support joins with the plurality of lengthwise supports at a place between of the distal and proximal end of the lengthwise supports.

In various embodiments, the lengthwise supports have a first generally straight configuration, and a second configuration, wherein both ends of the lengthwise supports bend radially outwardly while at least one place between the two ends remain unchanged.

In various embodiments, the device further comprises a plurality of first retrieval struts, wherein a distal end of the first retrieval struts joins with the proximal end of the lengthwise supports. In various embodiments, while in its first configuration, the first retrieval struts generally align with and are proximal to the lengthwise supports; and while in its second configuration, the distal ends of the first retrieval struts are radially outward from the proximal end of the first retrieval struts.

In various embodiments, the device comprises a plurality of second retrieval struts, wherein the distal ends of the second retrieval struts join the distal end of the lengthwise supports.

DETAILED DESCRIPTION

Figure 1:
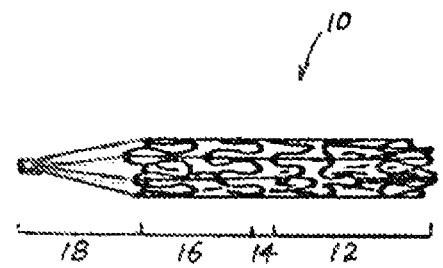
FIG. 1 is a perspective view of an exemplary pressure regulating device in accordance with certain embodiments of the present teachings.

The present teachings are described more fully herein with references to the accompanying drawings, which show certain embodiments of the present teachings. The present teachings may, however, be embodied in many different forms and should not be construed as being limited to the embodiments set forth herein. Rather, these embodiments are provided to illustrate various aspects of the present teachings. Like numbers refer to like elements throughout.

The present teachings provide devices and methods of use thereof. For example, the device can be used to regulate the pressure in a heart chamber. Specifically, the device can be used to (a) change an elevated chamber pressure or/and (b) prevent embolization from the right to left atria in a patient who suffers from CHF or has a Patent Foramen Ovale (PFO) or an Atrial Septal Defect (ASD) but needs a residual flow between the atria so as not to traumatize the heart hemodynamics.

As used herein, when the terms "distal" and "proximal" are used to refer portion of the device, they refer to a device in its elongated deliver configuration or its expanded deployed configuration. The term "proximal" shall mean close to the operator (less into the body) and "distal" shall mean remote from the operator (further into the body). In positioning a medical device from a downstream access point, "distal" is more upstream and "proximal" is more downstream.

As explained in further detail below, various embodiments of the present teachings provide medical devices for regulating the pressure in a heart chamber. In some embodiments, a medical device according to the present teachings includes a middle portion coupled by two retention flanges. In some embodiments, a medical device is positioned through an aperture in a septum, for example, between the left and right atria. In some embodiments, the two retention flanges of the medical device are disposed on the opposite sides of the septum. In some embodiments, a medical device according to the present teachings is extended into an elongated profile for a percutaneous delivery and resume the preset profile in vivo after deployment. As used in this application, unless otherwise indicated, the term "aperture" refers to any anatomical anomalies such as PFO, ASD, VSD, or an anatomical feature created for the purpose of creating a shunt.

An embodiment of the device in the present teachings has a distal portion configured to be positioned inside the left atrium, a proximal portion configured to be positioned inside the right atrium, and a middle portion between the distal and proximal portion and configured to fit inside an aperture on the atrial septum. In some embodiments, such configurations secure the device in place. Upon deployment, the device creates a conduit for blood to flow through. The distal portion and proximal portion of the device is designed to have a minimal contact with the septum. One of the results is that potential tissue erosion can be prevented.

An embodiment of the device includes a retrieval portion. In some embodiments, the retrieval portion connects to the distal portion of the device. In an alternative embodiment, the retrieval portion connects to the proximal portion of the device. In another embodiment, the retrieval portion is configured to be connected to a delivery system during delivery and/or implantation, and optionally to a retrieval system during retrieval.

An embodiment of a device in the present teachings has an elongated profile for delivering through a catheter system and an expanded profile to secure the device across the atrial septum. In some embodiments, the device is configured to transition from a delivery profile to a deployed profile through self-expansion or mechanical actuations. In some embodiments, during deployment, both the distal, proximal, and retrieval portions of the device expand radially while the device contracts longitudinally. In certain embodiments, one or both the distal, proximal, and retrieval portions of the device contract longitudinally. In various embodiments, one of or both the deployed distal and proximal portions has a generally frusto-conical shape. When a device is deployed and optionally released, the retrieval portion radially expands. In some embodiments, the deployed retrieval portion extends beyond the deployed device proximally or distally. In an alternative embodiment, the deployed retrieval portion is contained within the profile of the deployed device.

In some embodiments, the deployed distal portion is configured to be positioned inside the left atrium, the deployed proximal portion is configured to be positioned inside the right atrium, and the deployed middle portion is conjured to be positioned across an aperture on the atrial septum. According to some embodiments, the deployed middle portion applies compression force to its surrounding septal tissue, thereby securing the device across the septum.

FIG. 1 illustrates an embodiment of the device (10) in an elongated delivery profile. According to some embodiments, the device (10) is generally straightened and is suitable for being delivered via a delivery system (not shown). As illustrated in FIG. 1, the elongated device has a generally tubular profile with a distal portion (12), a middle portion (14), a proximal portion (16), and a retrieval portion (18). According to some embodiments of the present teachings, the device (10) in the delivery configuration has a generally tubular profile; and, when deployed in vivo, is configured to allow blood to flow from one side to the other.

Figure 2A:
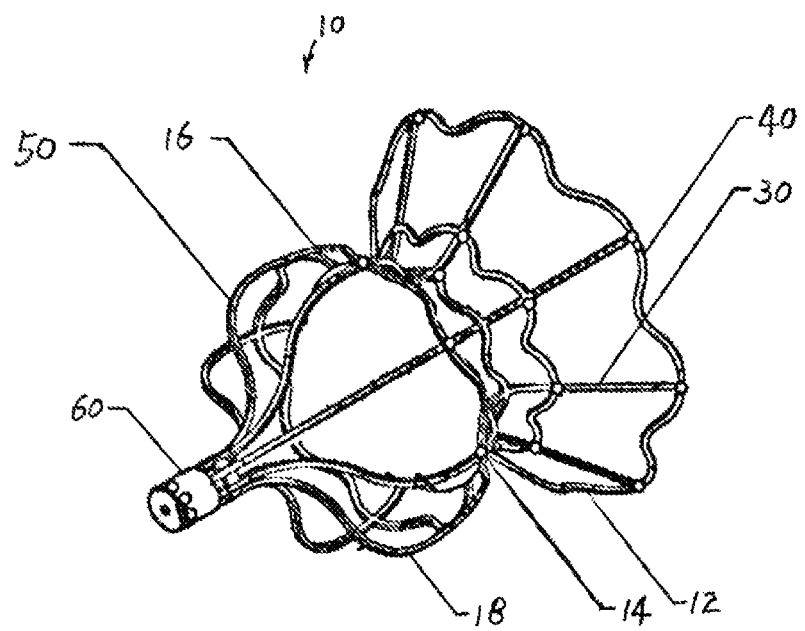
FIGS. 2A-2B are perspective views of the exemplary pressure regulating device of FIG. 1 in accordance with certain embodiments of the present teachings.
Figure 2B:
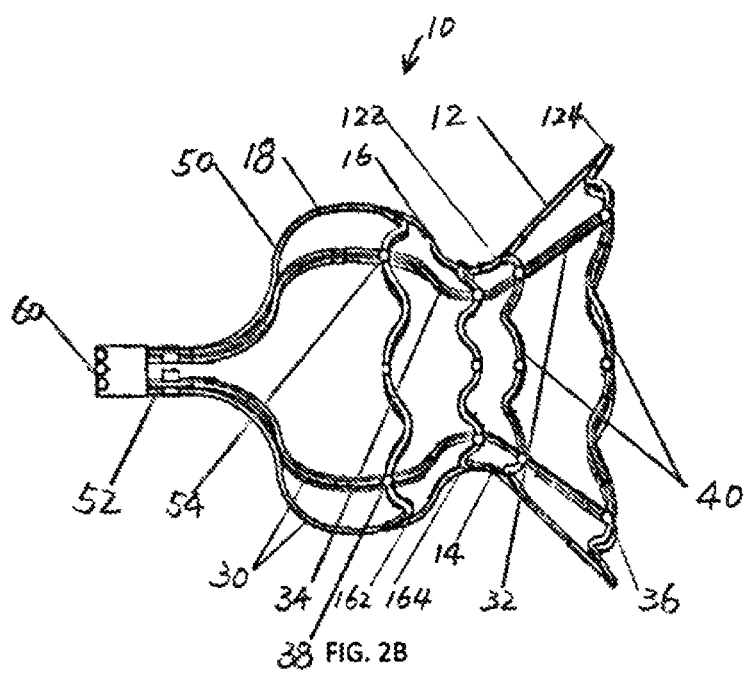

FIGS. 2A-2B illustrate an embodiment of the device (10) in a radially expanded deployed profile. As illustrated, according to some embodiments, all portions of the device (10) are radially expanded and axially shortened. According to some embodiments, as the device (10) expands from its delivery profile, the overall length of the device (10) reduces, sometimes significantly. In certain embodiments, the distal portion (12) of the device (10) includes a flared section with an increasing outside diameter (O.D.) from a proximal end (122) to a distal end (124) to form a general frusto-conical shape. In certain embodiments, the proximal portion (16) includes a flared section having a decreasing O.D. from a proximal end (162) to a distal end (164) to form a general frusto-conical shape.

Continuing referring to FIG. 2A, the middle portion (14) between the distal (12) and proximal portions (16) defines a narrowest part (smallest O.D.) of an internal passageway of the implantable retrievable device (10). According to some embodiments, the middle portion (14) of the device is a narrow interface where the distal and proximal portions meet. In certain embodiments, the middle portion (14) has a minimum longitudinal length. According to an alternative embodiment, the middle portion (14) has a small tubular profile with one end joining the distal portion and the other end joining the proximal portion. According to some embodiments, the middle portion (14) in the delivery configuration collapses radially and elongates axially (for example, comparing to that in its deployed configuration). Alternatively, the middle portion (14) of the device (10) in the delivery configuration remains generally the same shape and size as that in its deployed configuration.

As shown in FIG. 2A, the device has a plurality of lengthwise supports (30) extending continuously from its distal end (124) of the distal portion (12), through the middle portion (14), and to the proximal end (162) of the proximal portion (16). As shown in FIGS. 2A-2B, the lengthwise supports (30) each has a relatively straight profile, and once deployed, assumes its pre-bent profile with both its distal (32) and proximal sections (34) bending radially outwardly to form a waist or a middle portion. In some embodiments, the lengthwise supports (30) each has a uniform thickness and/or width throughout. In another embodiment, the lengthwise supports (30) have varying thickness and/or width throughout its length. In some embodiments, the lengthwise supports (30) have a uniform rigidity throughout. In other embodiments, the lengthwise supports (30) have varying rigidity and/or flexibility throughout. For example, the lengthwise supports (30) can have a thicker and/or wider section that forms a waist at the middle portion (14) of the deployed device (10). The thickness/width difference can result a relatively stiffer middle portion (14) of the device (10) in order to compress the surrounding tissue and secure the device (10); and a relatively flexible distal and proximal portion of the device in order to avoid accidental tissue erosion. In some embodiments, the thickness and/or width of the lengthwise support ranges from about 0.005 inch to about 0.030 inch. In some embodiments, the number of lengthwise supports (30) is any number between 3 and 12. One skilled in the art should also understand that the relatively stiff middle section and relatively flexible distal (32) and proximal sections (34) of the lengthwise supports (30) can also be achieved by varying the material or its property.

Figure 3A:
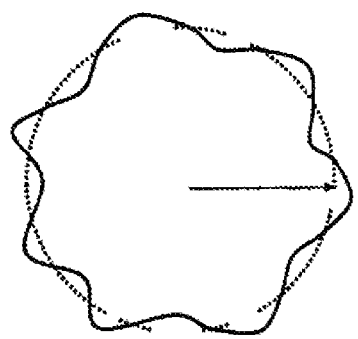
FIGS. 3A-3B are planary views of the exemplary pressure regulating device of FIGS. 2A-2B in accordance with certain embodiments of the present teachings.
Figure 3B:

The device (10) has a plurality of perimeter supports (40) connected to at least two of the lengthwise supports (30). According to another embodiment, each perimeter support (40) joins the lengthwise supports (30) it comes across in order to avoid metal rubbing. Each of the perimeter support (40) has a noncircular shape to allow each to become compressed into a smaller radius and be inserted into the delivery catheter (74) for percutaneous delivery. FIG. 3A is a plan view of the shape of a perimeter support (40) according to some embodiments of the present teachings. Other shapes are possible. As shown, the perimeter support (40) varies from a circular shape by a deviation around its perimeter. This deviation may be a regular offset in the radial direction from a circular shape. The deviation may increase in radius from the circular shape then decrease in radius from the circular shape around the perimeter of the circle. FIG. 3B is a side elevational view of a perimeter support (40). As shown in FIG. 3A, the longitudinal direction is perpendicular to the radial direction and the perimeter supports (40) have a deviation from a flat plane in a positive longitudinal direction followed by a deviation from a flat plane in a negative longitudinal direction. Since the perimeter support (40) does not lie in a single plane, it can be more easily collapsed. This allows for the device (10) to be compressed and packed into a catheter for insertion or removal. According to some embodiments, there are at least 4 perimeter supports (40) on the device (10), one joining the distal ends (36) of the all lengthwise supports (30), another one joining the proximal ends (38) of the all lengthwise supports (30), and the other two near each ends of the middle portion (14) of the device (10) in order to provide additional stiffness to the middle portion (14) of the device (10). One skilled in the art should understand that more or less perimeter supports (40) could be incorporated into the device (10) and/or the proximal (16) and distal portions (12) of the device (10) could join different numbers of perimeter supports (40). Thus the exemplary embodiment shown in the figures should not be viewed as limiting.

In some embodiments, all perimeter supports (40) have a same rigidity. In other embodiments, one perimeter support (40) has different rigidity and/or flexibility than another perimeter support (40). For example, the perimeter support (40) near each end of the middle portion (14) of the device (10) can have a relatively thicker and/or wider profile and the perimeter support (40) at each end of the lengthwise supports (30) can have a relatively thinner and/or narrower profile. The thickness/width difference would result in a relatively stiffer middle portion (14) (for example, for the device to compress the surrounding tissue and secure the device in place); and a relatively flexible distal and proximal ends (for example, for the device to avoid accidental tissue erosion). In some embodiments, the thickness and/or width of the perimeter support (40) could range from 0.005 inch to about 0.030 inch. Similar to what has been disclosed above, one skilled in the art should also understand that the relative stiffness could also be achieved by varying the material or/and its property.

FIGS. 2A-2B further illustrate a retrieval portion (18) according to an aspect of the present teachings. In various embodiments, the retrieval portion (18) joins the proximal portion (16) of the device (10). The retrieval portion (18) also includes a plurality of struts (50). The distal ends (54) of the struts (50) join the proximal ends (162) of the proximal portion (16). The distal end (54) of the struts (50) meet each other at a location near the axial center of the device (10). As illustrated in the figures, a fully deployed proximal portion (16) can have a conical shape with its distal end (164) having the smallest diameter and its proximal ends (162) having the largest diameter. Also as illustrated in the figures, the distal end (164) of the proximal portion (16) joins the middle portion (14) of the device (10). One skilled in the art should understand that in the event where a fully deployed device (10) has to be retracted into a delivery sheath (72), the radially expanded proximal end (162) of the proximal portion (16) poses a hurdle. With the retrieval struts (50) joining the proximal ends (162) of the proximal portion (16), pulling the proximal struts (50) would then lead to radially collapsing of the proximal portion (16), thereby reducing its radial profile and allowing it to be retracted into the distal end of the delivery sheath (72).

Optionally, a proximal hub (60) connects to all the distal ends (54) of the retrieval struts (50), as shown in FIG. 2A. This retrieval portion (18), optionally the proximal hub (60) at the proximal end of the retrieval portion (18), allows a catheter to attach to it during the deployment process. All attachment mechanism known to those skilled in the field could be incorporated for the attachment between the proximal hub and the catheter. Examples such as screw, collet, pin-hole, suture, and etc. could all be used herein. This would allow a clinician to assess the deployment of the device (10) before the clinician fully releases the device (10). The retrieval portion (18) of the device (10) also allows the device (10) to be re-attached to a retrieval system should a clinician decide to remove the device (10) from the patient.

Figure 6:
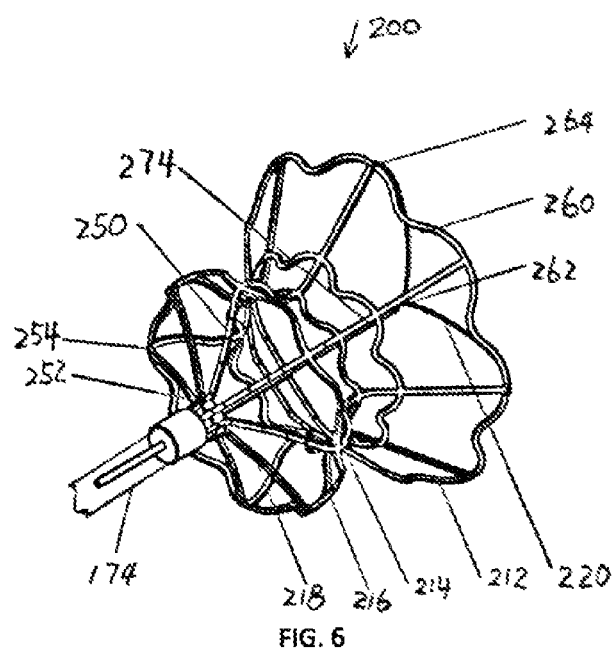
FIG. 6 is a perspective view of another exemplary pressure regulating device in accordance with certain embodiments of the present teachings.

According to some embodiments, the retrieval portion (18) joins the proximal portion (16) of the device (10) as illustrated in FIGS. 1-3. In other embodiments, the retrieval portion (18) joins the distal portion (12) of the device (10). In yet other embodiments, the device has two retrieval portions, where the first one joins the proximal portion of the device and the second one joins the distal portion of the device, as shown in FIG. 6.

According to some embodiments of the present teachings, as shown in FIG. 2A, at least one lengthwise support (30) extends past the proximal flared portion (16), curves back towards a centerline, and forms the retrieval strut (50). In some embodiments, the number of retrieval struts (50) is the same as that of the lengthwise supports (30). Alternatively, there are less retrieval struts (50) than the lengthwise supports (30). In some embodiments, at least one retrieval strut (50) is an extension of the lengthwise supports (30). Alternatively, all retrieval struts (50) are independent of the lengthwise struts (50). In some embodiments, the retrieval struts (50) connect the proximal ends (162) of the proximal flared portion (16) with equal spacing between every two struts (50). In some embodiments, the number of retrieval struts (50) is any number between 3 and 12.

Figure 4:
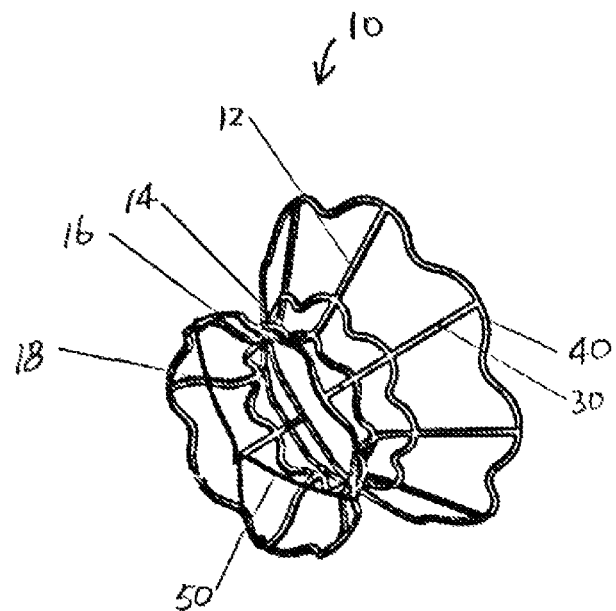
FIG. 4 is a perspective view of another exemplary pressure regulating device in accordance with certain embodiments of the present teachings.

Upon deployment and release, the retrieval struts (50) extend radially inwardly from the most radially outward end of the proximal portion of the device (10) toward the axial center of the device (10). According to some embodiments, the deployed retrieval portion (18) has a profile that extends proximally beyond the proximal portion (16) and has a shape similar to a cone, a wine glass, and the like, for example, as shown in FIG. 2A. According to other embodiments, the deployed retrieval portion (18) is contained within the space inside the deployed proximal portion (16) of the device (10), for example, as shown in FIG. 4. In these embodiments, some of the deployed retrieval portion (18) has a small longitudinal profile. One skilled in the art should understand that other configurations of the retrieval portion (18) could also be incorporated to allow a device (10) to be retrieved and repositioned.

According to one embodiment, the retrieval struts (50) are configured to allow a clinician to control the device (10). In various embodiments, the distal and proximal portions (16) are fully deployed in vivo and the device (10) does not experience any excess stress caused by its connection to a delivery catheter (74). In another embodiment, the retrieval struts (50) are configured to allow the device (10) to be pulled back into a retrieval catheter smoothly without any part of the device (10) being caught by the distal end of the catheter. In another embodiment, the retrieval struts (50) are configured to minimize the retrieval force required for pulling the device (10) back into a catheter. Thus, according to some embodiments, the length of the retrieval struts (50) vary depending on the overall size of the device and the ability of the device to achieve the above-mentioned functions. In some embodiments, the retrieval struts (50) have the same size and profile as the lengthwise supports (30). In other embodiments, the retrieval struts (50) have a different size or/and a different profile as the lengthwise supports (30).

In one embodiment, the width and the thickness of the lengthwise supports (30) are the same. In another embodiment, the width of at least one of the lengthwise supports (30) is greater than the thickness. In one embodiment, the width and the thickness of the retrieval struts (50) are the same. In another embodiment, the width of at least one of the retrieval struts (50) is greater than the thickness. In some embodiments, the curving and bending of at least one of the retrieval struts (50) is achieved in a controlled manner. In certain embodiments, twisting of a strut during the process is prevented. According to some embodiments, the thickness of the lengthwise supports (30) and retrieval struts (50) ranges from about 0.003" to about 0.09".

Figure 5A:
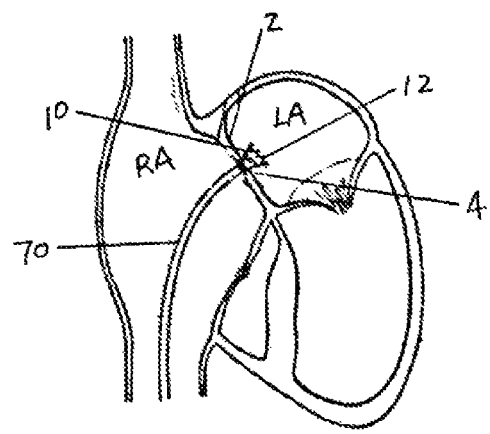
FIGS. 5A-5C illustrate an exemplary delivery system deploying an exemplary pressure regulating device across the atrial septum.
Figure 5B:
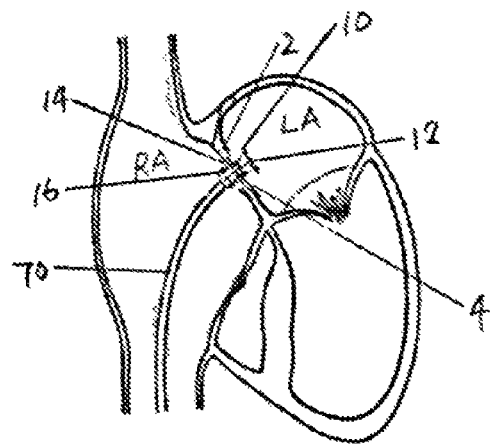

According to some embodiments, the retrieval portion (18) is configured to be attached to a delivery system. One skilled in the art would understand that a clinician can use such a delivery system to deploy the device (10) at a treatment location, sometimes even fully, while still maintain control of the device (10). By doing so, the clinician can assess the deployment of the device (10) and retrieve it if it becomes necessary. In one embodiment, such as shown in FIGS. 5A-5B, a delivery catheter (74) attaches to the proximal end of the retrieval portion (18), either through a proximal hub (60) at the end of the retrieval struts (50) or other mechanism. Upon deployment, the delivery catheter (74) releases the retrieval portion (18) of the device (10).

The device (10) is deployed across the atrial septum (2), with the distal portion (12) extending into the left atrium and the proximal portion (14) extending into the right atrium. In some embodiments, this configuration minimizes tissue growth on each portion. In various embodiments, the deployed device (10) includes an enlarged opening (20) in the middle portion (14) and the opening (20) extends from one end of the device (10) to the other. In some embodiments, the opening (20) is used for blood to flow from one side of the device (110) to the other. According to one embodiment, when the device (10) is deployed in vivo, the radial spans of both the distal (12) and proximal portions (16) are designed to minimize its contact with the atrial septum (2) and surrounding cardiac structures.

In some embodiments, as the device (10) is deployed across the atrial septum (2), the deployed distal portion (12) has a same shape and/or profile as the deployed proximal portion (16). In another embodiments, the deployed distal portion (12) has a different shape and/or profile as the deployed proximal portion (16). For example, one of the distal and proximal portions could have a cone shape and the other could have a cup shape. In another embodiment, one of the distal and proximal portions has a longer length and narrower flare angle than the other. According to some embodiments, the angle in which the distal and/or proximal portion flares outwardly from the central axis is between about 60° to less than about 90°. One skilled in the art should understand various shapes, profiles, or/and sizes could be incorporated herein and each exemplary embodiment illustrated or described should not be viewed as limiting.

In some embodiments, as the device (10) is deployed across the atrial septum (2), the deployed distal portion (12) has the same size as the deployed proximal portion (16). In other embodiments, as the device (10) is deployed across the atrial septum (2), the expanded distal portion (12) of the device (10) is slightly larger radially than the expanded proximal portion (16). In certain embodiments, the size difference is to account for the typical left-to-right transatrial pressure gradient and to facilitate deployment. In some embodiments, the distal end of the deployed distal portion (12) of the device has the largest diameter upon deployment. In certain embodiments, the distal end (124) of the deployed distal portion (12) has a diameter of about 8-20 mm. In another embodiment, the proximal end (162) of the deployed proximal portion (16) of the device (10) has the largest diameter upon deployment. In certain embodiments, the proximal end (164) of the deployed proximal portion (16) has a general diameter of 8-20 mm upon deployment. According to some embodiments, upon deployment, the diameter of the deployed middle portion (14) of the device (10) is about 25-50% of the diameter of the deployed distal portion (12).

As shown in FIG. 1, the middle portion (14) is the narrowest portion of a deployed device (10). According to some embodiments, when the device (10) is deployed in vivo, the radially expanded middle portion (14) of the device (10) is configured to apply a compression force toward the surrounding heart tissues at the aperture by its outside tubular surface. When the device (10) is deployed across an aperture in the atrial septum (2), the aperture would generally cause the device (10) to move in a direction such that the atrial septum (2) fits onto the narrowest portion of the device (10). For example, if the device (10) is implanted with the distal flared portion (12) contacting the atrial septum (2), because the interatrial septum (2) has the tendency of reducing its size, the force that the interatrial septum (2) exerts on the flared portion would cause the device (10) to move until the middle portion (14) is located at the interatrial aperture. Similarly, if the device (10) is positioned such that the proximal flared portion (16) is located in the interatrial aperture, the same force would move the device (10) until the middle portion (14) is located at the interatrial aperture. This causes a self-centering effect and reduces the occurrence of the device (10) moving out of the atrial septum (2) aperture.

According to some embodiments, the device (10) in its collapsed form may be loaded into a catheter for percutaneous delivery into the heart and implantation in an aperture in the atrial septum (2). Each perimeter support (40) has a noncircular shape that allows the perimeter support (40) to be compressed into a smaller radius and inserted into the delivery catheter (74). In these embodiments, the device (10) is stretched longitudinally and loaded into a deliver catheter. Upon the device (10) being stretched longitudinally, the cross-sectional diameters of the device (10) transition into smaller dimensions than the respective deployed diameters. Accordingly, in various embodiments, the device (10) has a first diameter for percutaneous deliver and a second diameter for deployment in the treatment location. One skilled in the art should understand that in the delivery profile, the lengthwise supports (30) or/and perimeter supports (40) pack tightly close to one another.

In some embodiments of the present teachings, the device (10) in its delivery configuration, such as illustrated in FIG. 1, is configured to be delivered and deployed through a 5 French-12 French catheter. In one embodiment, the cross section of the elongated device (10) has a diameter ranging from about 1-4 mm. In certain embodiments, the cross section of the middle portion (14) in a deployed configuration has a diameter ranging from about 3-12 mm, or from about 110% to about 300% of that of the middle portion (14) in a delivery profile.

In some embodiments of the present teachings, the device (10) in its delivery configuration, such as illustrated in FIG. 1A, has an overall length of about 5-25 mm, with the length of the middle portion (14) being 0.5-5 mm. In one embodiment, for a deployed device (10), the length of the middle portion (14) ranges from about 1-3 mm, with the overall length of the device (10) ranging from about 3-12 mm. In another embodiment, the length of the middle portion (14) of a deployed device ranges from about 5 to about 16% of the length of the deployed device (10).

According to one embodiment, while the device (10) is in its delivery configuration, the distal portion (12) collapses radially. According to one embodiment, while the device (10) is in its deployed configuration, the distal portion (12) expands radially with the lengthwise supports (30) bending radially outwardly at a pre-defined angle. Upon the device (10) being deployed in vivo, the distal portion (12) is configured to be in a generally frusto-conical shape and extends into the left atrium. According to some embodiments, the length of the distal cone portion of the deployed device has a length of about 3-10 mm. According to certain embodiments, the proximal end (122) of the deployed distal portion (12) joins the middle portion (14) and the distal end (124) of the deployed distal portion (12) has a general diameter of about 8-20 mm.

According to one embodiment, while the device (10) is in its delivery configuration, the proximal portion (12) collapses radially. According to one embodiment, while the device (10) is in its deployed configuration, the proximal portion (16) expands radially with the lengthwise supports (30) bending radially outwardly at a pre-defined angle. Upon the device (10) being deployed in vivo, the proximal portion (12) is configured to be in a generally frusto-conical shape and extends into the right atrium. According to some embodiment, the length of the deployed proximal cone portion (16) has a length of about 3-10 mm. According to certain embodiments, the distal end (164) of the deployed proximal portion (16) joins the middle portion (14) and the proximal end (162) of the deployed proximal portion (16) has a general diameter of about 8-20 mm.

In various embodiments, the device (10) is fabricated from a tube. Thus, all portions of the device (10), such as the distal portion (12), the middle portion (14), the proximal portion (16), and retrieval portion (18), have a same thickness. In one embodiment, the thickness of the tube, and thus the thickness of each portion of the device (10), is from about 0.005 inch to about 0.007 inch. In another embodiment, at least one portion of the device (10) has a different thickness than the rest of the device (10). This, in some circumstances, can be achieved by removing some material from one or more portions of the device. One skilled in the art should understand that the device can be fabricated by laser cutting or other method known to those skilled in the art.

According to some embodiments, the deployment of an exemplary device (10) inside the heart of a patient starts with locating an aperture in the atrial septum (2). In the event where no aperture exists in the atrial septum (2), one can be created, for example, by puncturing the atrial septum (2). Septal puncture procedures are well known to those with ordinary skill in the art. According to some embodiments, after an aperture is created, a guide wire, not shown, is placed across the aperture (4) to guide the delivery and deployment of a device of the present teachings. Alternatively, the delivery assembly (70) can be used to deliver and deploy a device without the need of a guide wire.

Upon locating the aperture (4), the delivery assembly (70) is inserted percutaneously into the right atrium through a standard right heart catheterization. According to some embodiments of the present teachings, the delivery assembly (70) includes a delivery sheath (72) with a proximal end (not shown), a distal end, and a longitudinal lumen extending in between, and the device (10) in its elongated delivery profile constrained inside the distal portion of the delivery sheath (72). The delivery assembly (70) further includes a delivery catheter (74) slidably disposed within the delivery sheath (72) and the distal end of the delivery catheter (74) is configured to attach to the retrieval portion (18) of the device (10). Once inside the right atrium, the distal portion of the delivery assembly (70) extends cross the aperture (4) in the septum (2) and enters the left atrium. In some embodiments, a radio-opaque marker is used on the delivery sheath (72) to aid a clinician in determining how far the distal portion of the delivery assembly (70) extends inside the left atrium. According to some embodiments, the device (10) is pre-loaded in the distal portion of the delivery sheath (72) and is carried across the atrial septum (2) as the delivery assembly (70) extends percutaneously. According to other embodiments, the delivery catheter (74) is positioned across the septum first, the device (10) is then pushed from the proximal end to the distal portion of the delivery sheath (72).

In various embodiments, a clinician starts the deployment of the device (10) by first deploying the distal portion (12) of the device (10) inside the left atrium, for example, by retracting the delivery sheath (72) proximally while holding the collapsed device (10) by the delivery catheter (74). In certain embodiments, as the distal portion (12) of the device (10) is exposed outside of the delivery catheter (74), the distal portion (12) of the device expands radially and contracts axially to assume its pre-set frusto-conical-shaped deployed configuration, as illustrated in FIG. 5A.

In various embodiments, the entire delivery assembly (70), including the delivery sheath (72), the delivery catheter (74) and the device (10) with its distal portion deployed outside of the delivery sheath (72) and its proximal portion (16) still constrained inside the delivery sheath (72), is retracted proximally, while the deployed distal portion (12) of the device (10) remains inside the left atrium.

According to some embodiments, the proximal portion (16) of the exemplary device (10) is deployed by using the similar steps as described above. According to one embodiment, after the distal end of the delivery assembly (70) is left inside the right atrium and the deployed distal portion (12) of the device (10) is left inside the left atrium, the delivery sheath (72) is withdrawn proximally to expose the proximal portion (16) of the device (10) inside the right atrium. In certain embodiments, the proximal portion (16) of the device (10) expands radially and contracts axially to assume its pre-set frusto-conical-shaped deployed configuration as shown in FIG. 5B.

According to one embodiment of the present teachings, during deployment of the proximal portion (16) of the device (10), the radial expansion of the proximal portion (16) is also accompanied by at least a partial radial expansion of the retrieval portion (18). As shown in FIG. 5B, according to some embodiments, the distal (12), middle (14), and proximal (16) portions are fully deployed at a treatment location and the retrieval portion (18) partially expands radially with the proximal ends (52) of the struts (50) remaining attached to the delivery system (70). As shown in FIG. 5B, as the distal portion (12) is located inside the left atrium, the middle portion (14) is located across the aperture (4), and the proximal portion (16) is located inside the right atrium, the device remains to be controlled by the clinician through the attachment between the delivery catheter (74) and the retrieval portion (18) of the device. In some embodiments, the clinician can assess the deployment of the device (10).

According to one embodiment, if the clinician is not satisfied with the deployment, the clinician retrieves the device (10). To retrieve the device (10), the clinician pulls the retrieval portion (18) proximally and extends the distal end of the delivery sheath (72) distally to cause the proximal ends (52) of the retrieval struts (50) to slide proximally into the delivery sheath (72). Because the retrieval struts (50) are connected with the proximal end (162) of the proximal portion (16), as the proximal struts (50) are pulled further proximally, the distal end of the delivery sheath (72) extends further distally and the proximal end (162) of the proximal portion (16 are pulled proximally. The extension of the delivery sheath (72) and pulling of the proximal end (162) of the proximal portion (16) collapses and allows the deployed proximal portion (16) to be retracted into the distal portion of the delivery sheath (72). The continue proximal pulling of the retrieval portion (18) and the distal advancing of the delivery sheath (72) further collapses and allows the distal portion of the device to be retracted into the distal portion of the delivery sheath (72). At this point, the clinician can remove the delivery system (70) and the device (10) from the body. Alternatively, the device (10) can be redeployed by following the steps described herein.

Although one particular retrieval method is described here, one skilled in the art would recognize that other retrieval methods can be incorporated without departing from the scope of the present teachings. For example, while the proximal end of the device (10) is engaged with the delivery assembly (70), a retrieval means can be advanced to retrieve the device (10).

Figure 5C:
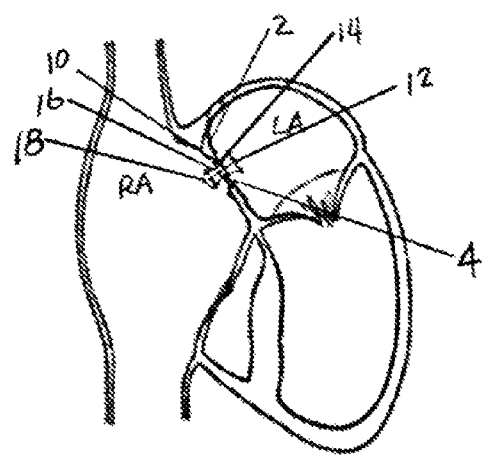

Upon completing deployment of the proximal portion (16) of the device (10), if the clinician is satisfied with the deployment, the device can be completely released. To do so, the clinician first releases the attachment between the delivery catheter (74) and the retrieval portion (18) of the device (10). After the device (10) is completely free of attachment, the delivery system (70) is removed from the patient. FIG. 5C depicts an embodiment of a fully deployed device (10) of the present teachings deployed across the atrial septum (2). The device (10) can be one of those shown in FIGS. 2A and 4. In certain embodiments, the device (10) is fully deployed with the distal portion (12) of the device (10) residing inside the left atrium, the proximal portion (16) residing inside the right atrium, the retrieval portion (18) assuming its pre-defined shape which also resides inside the right atrium, the middle portion (14) residing across the aperture (4) in the septum (2). In particular embodiments, the device (10) is secured in place. According to some embodiments of the present teachings, the deployed device (10) creates a conduit for blood to flow from one chamber of the heart to another by going through the opening (20). As the left atrial pressure is typically higher than the right atrial pressure, the blood is therefore, typically shunting from the distal portion of the device, through the middle portion, and exiting from the proximal and retrieval portions of the device.

FIG. 6 illustrate another embodiment of the present teachings. In this embodiment, the device (200) includes a distal portion (212), a middle portion (214), a proximal portion (216), and two retrieval portions (218, 220). In some embodiments, the device (200) includes a first retrieval portion (218) joining the distal portion (212). In some embodiments, the device (200) includes a second retrieval portion (220) joining the proximal portion (216). Similar to the retrieval portion (18) described above, both the first and second retrieval portion (220) have multiple retrieval struts (250). As shown in FIG. 4, the distal end (254) of each retrieval strut (250) of the first retrieval portion (218) joins the proximal end of the proximal portion (216). The proximal ends (252) of the retrieval struts (250) extend to a location near the axial center of the device (200). The distal end (254) of each retrieval strut (250) of the second retrieval portion (220) joins the distal end of the distal portion (212).

The proximal ends (252) of the retrieval struts (250) extend to a location near the axial center of the device (200). At least one of the distal (212), proximal (216), and middle portions (214) of this embodiment has similar or the same characteristics as the distal (12), proximal (16), and middle (14) portions of the various embodiments described above, including varying profile, shape, size, flexibility, thickness, width, etc. At least one of the first and second retrieval portions (220) of this embodiment has similar or the same characteristics as the corresponding retrieval portion (18)s of the various embodiments described above, including varying profile, shape, size, flexibility, thickness, width, etc.

The retrieval struts (250) in the first retrieval portion (218) function similarly to the retrieval struts (250) described in certain embodiments discussed herein. It provides an attachment between the device (200) and a delivery catheter during the deployment process. It also allows a clinician to control the device (200) as well as assess the positioning of the device (200) at the treatment location before releasing the device completely. It also facilitates the retrieval of a deployed device by radially collapsing the proximal portion (216) of the device (200) and assisting the proximal portion (216) of the device (200) to re-enter the distal end of the delivery sheath (72).

The retrieval struts (260) in the second retrieval portion (220) are connected with the distal ends of the distal portion (212) of the device (200). The second retrieval portion (220) also functions similarly to the first retrieval portion (218). Specifically, a clinician can use the second retrieval portion (220) to maintain contact or/and control of the device (200), to control the deployment of the distal portion (212) of the device (200). In certain embodiments, the clinician can use the struts (260) of the second retrieval portion (220) to actuate the deployment of the device (200). In certain embodiments, the proximal retraction of the second retrieval portion (220) initiates the radial collapse of the distal portion (212) of the device (200) and reduces the force required to retract the entire device (200) into the delivery sheath (72).

In various embodiments, as illustrated in FIG. 6, the device (200) has a first retrieval portion (218) releasably connected with a first delivery catheter (174) and a second retrieval portion (220) releasably connected with a second delivery catheter (274). As shown in FIG. 5, the second delivery catheter (274) is inside the axial space of the device (200). In some embodiments, as the device (200) transitions to its delivery profile, the distal portion (212) of the device (200) collapses radially and the struts (50) of the second retrieval portion (220) contract radially. According to one embodiment of the present teachings, the delivery assembly of the current embodiment includes a first delivery catheter (174) releasably connected with the proximal ends of the first retrieval portion (218), a second delivery catheter (274) releasably connected with the proximal ends of the second retrieval portion (220), and a collapsed device (200). In such a delivery catheter assembly, the first delivery catheter (174) is positioned proximally to the collapsed device (200), and the second delivery catheter (274) slidably disposed within an axial lumen of the first delivery catheter (174) and within the luminal space within the collapsed device (200). The distal end of the second delivery catheter (274) is positioned distally to the distal end of the first delivery catheter (174). Such a delivery catheter-device assembly is then placed inside a delivery sheath (172) which would deliver the device percutaneously to the treatment location.

Although what has been described herein is an embodiment of the present teachings where the second delivery catheter (274) is slidably disposed within an axial lumen of the first delivery catheter (174) as shown in FIG. 6 and the first delivery catheter (174) is slidably disposed within an axial lumen of the delivery sheath (172), one skilled in the art should understand that other designs can also be used to achieve the same goal. For example, both the first (174) and second (274) delivery catheters can be slidably disposed side-by-side in the same lumen of the delivery sheath (172), along with the device in it delivery profile.

According to some embodiments, the struts (260) of the second retrieval portion (220) are more rigid than the struts (250) of the first retrieval portion (218). This, in certain embodiments, allows the distal portion of the device (200) to be pushed by the first delivery catheter (174), for example, outside of the delivery sheath (172) during the delivery. In another embodiment, the struts (260) on the second retrieval portion (220) are more flexible than those of the first retrieval portion (218). In certain embodiments, the struts (260) on the second retrieval portion (220) allow the distal end of the distal portion (212) of the device (200) to be pulled during a retrieval.

According to some embodiments, the struts (250, 260) of the first and second retrieval portions (218, 220) have the same profile, shape, length, thickness, width, and material. Alternatively, the struts (250, 260) of the first and second retrieval portions (218, 220) have different profiles, shapes, lengths, thicknesses, widths, and materials from each other. One skilled in the art should understand the variations in each perimeter (for example, profile, shape, length, thickness, width, or material) could lead to variations in device design and variations in device implantation behavior. All variations are within the scope of the present invention.

In various embodiments, the deployment of the embodiment as shown in FIG. 6 also starts with locating and placing a delivery assembly across an aperture in the atrial septum (2). In some embodiments, the distal end of the delivery assembly is extended inside the left atrium. Once in place, the distal portion (212) of the device (200) is exposed inside the left atrium. In some embodiments, the distal portion (212) of the device (200) expands radially to resume its pre-defined conical shape. In certain embodiments, the expansion is achieved when the second retrieval portion (220), and thus the distal end (212), is pushed by a second delivery catheter (274). In certain embodiments, the expansion is achieved by self-expansion. In particular embodiments, the design and/or the material of the device (200) has the ability to cause the device (200) to resume its pre-formed shape. The deployment of the distal portion (212) of the device (200) also leads to a radial expansion of the struts (260) and/or a distal movement of the second delivery catheter (274) in relation to the first delivery catheter (174).

While the second delivery catheter (274) is being held steady, the proximal portion (216) is exposed or extends outside the delivery system and inside the right atrium. Similar to the deployment of the distal portion (212), in some embodiments, the proximal portion (216) of the device (200) expands radially to resume it pre-defined conical shape. In certain embodiments, the expansion is achieved when the first retrieval portion (218), and thus the proximal end, is pushed by a first delivery catheter (174). In certain embodiments, the expansion is achieved by self-expansion. In particular embodiments, the design and/or the material of the device (200) has the ability to cause the device (200) to resume its pre-formed shape. The deployment of the proximal portion (216) of the device (200) also leads to radial expansion of the second retrieval struts (260) and/or a distal movement of the first delivery catheter (174) in relation to the second delivery catheter (274).

In various embodiments, after the deployment of the device (200), a clinician assesses the deployment of the device (200). Should the clinician is satisfied with the deployment, the clinician releases the device (200) by disengage the first and second delivery catheters (174, 274) with the first and second retrieval portions (218, 220) of the device (200). If the clinician is not satisfied with the deployment, the clinician retrieves the device (200). To retrieve the proximal portion (216) of the device (200), similar to the previously described steps, the clinician pulls the proximal ends (262) of the retrieval struts (260) to allow them to slide proximally back into the delivery sheath (172). The proximal ends of the proximal portion (216) also collapse radially and are pulled proximally into the distal portion of the delivery sheath (172). The distal portion (212) of the device (200) can be retrieved in the same manner as the proximal portion (216). While the clinician continues pulling the first retrieval portion (218) proximally, the clinician also pulls the second catheter (274) proximally to collapse the second retrieval struts (260). As a result, the distal portion (212) of the device (200) collapses radially and slides into the distal portion of the delivery sheath (172). During this process, the delivery sheath (172) can be held steady, or advanced distally. At this point, the clinician can remove the delivery system and the device (200) from the body. Alternatively, the device (200) can be redeployed by following the similar steps described herein.

The exemplary techniques for deploying the embodiments described herein are solely for illustration. It should be understood that other techniques can be used instead of, or in combination with, these exemplary techniques, because a clinician can select a technique to deploy an embodiment of the present teachings based on the particular features of the device, the delivery system, and the anatomy in which the device is being deployed.

According to one embodiment, the embodiments disclosed in the present teachings is manufactured by laser cutting a biocompatible metal tube. According to some embodiments, the device is made of a biocompatible metal or polymer. In various embodiments, the entire device is made of a biocompatible metal or polymer. In some embodiments, the device in its entirely or portion(s) thereof, for example, those with curved/bent deployment configuration, is made of an elastic material, a super-elastic material, or a shape-memory alloy so that the above portions can be distorted into a generally straightened profile during the delivery process and resume and maintain its intended profile in vivo once it is deployed from a delivery catheter (74). In some embodiments, the device is made of stainless steel, nitinol, Titanium, Elgiloy, Vitalium, Mobilium, Ticonium, Platinore, Stellite, Tantalum, Platium, Hastelloy, CoCrNi alloys (e.g., trade name Phynox), MP35N, or CoCrMo alloys, any other metallic alloys, or a mixture thereof. Alternatively, in some embodiments, a part of the device or the entire device is made of a polymer, such as PTFE, UHMPE, HDPE, polypropylene, polysulfone, or other biocompatible plastic. The surface finish of the device can be textured to induce tissue response and tissue ingrowth for improved stabilization. Alternatively, a part of or the entirety of the device can be fabricated from a resorbable polymer. In some embodiments, the resorbable polymer includes polylactic acid, polyglycolic acid, polycaprolactone, a combination of two or more of the above or a variety of other resorbable polymers that are well known to those skilled in the art.

According to one embodiment of the present teachings, the device is fabricated from a tubular form and then shaped to its final configuration. In one embodiment, if a sufficiently elastic and resilient material, such as nitinol, is used, the structure is preformed into the finished shape and elastically deformed. In some embodiments, the device is stowed in a delivery device during the delivery and the device elastically recovers its shape upon deployment. In some embodiments, one, some, or all portions of the device are manually expanded to the desired diameter and/or curved to a pre-set shape. In certain embodiments, one, some, or all portions of the device is heat set in an oven while constrained to the desired shape.

According to one embodiment of the present teachings, at least one portion of the device expands radially upon being deployed in vivo. According to one embodiment of the present teachings, upon deployment, the radial expansion of at least one portion of the device is due to the elastic nature of the material. According to another embodiment of the present teachings, upon deployment, the radial expansion of at least one portion of the device is due to its pre-set thermal shape memory of the material. According to yet another embodiment of the present teachings, during deployment, at least one portion of the device is manually expanded radially via a balloon.

According to various embodiments of the present teachings, one or more radio-opaque markers are used. Without attempting to limit to any particular function, these radio-opaque markers can be visualized by using radiographic imaging equipment such as X-ray, magnetic resonance, ultrasound, or other imaging techniques known to one of ordinarily skilled in the art. One or more markers as disclosed herein can be applied to any part of a device or a delivery system of the present teachings. A radio-opaque marker can be weld, sewed, adhered, swaged riveted, otherwise placed, and secured in or on the device. The radio-opaque marker may be made of tantalum, tungsten, platinum, iridium, gold, or alloys of these materials or other materials that are known to those skilled in the art. The radio-opaque marker can also be made of numerous paramagnetic materials, including one or more elements with atomic numbers 21-29, 42, 44, and 58-70, such as chromium (III), manganese (II), iron (III), iron (II), cobalt (II), copper (II), nickel (II), praseodymium (III), neodymium (III), samarium (III), ytterbium (III), gadolinium (III), terbium (III), dysprosium (III), holmium (III) and erbium (III), or other MR visible materials that are known to those skilled in the arts.

The methods and devices disclosed herein are useful for treating various symptoms of heart failures, in particular diastolic heart failures, by reducing the pressure in the left atrium and pulmonary veins. One skilled in the art would further recognize that devices according to the present teachings could be used to regulate pressure in other parts of the heart and/or vascular portions of the body. For example, the devices disclosed herein can be deployed on the septum between the left and right atria, the left and right ventricles, the left atrium and the coronary sinus, and the like.

Various embodiments have been illustrated and described herein by way of examples, and one of ordinary skill in the art would recognize that variations can be made without departing from the spirit and scope of the present teachings. The present teachings are capable of other embodiments or of being practiced or carried out in various other ways. Also, it is to be understood that the phraseology and terminology employed herein are for the purpose of description and should not be regarded as limiting.

Unless otherwise defined, all technical and scientific terms used herein have the same meaning as commonly understood by one of ordinary skill in the art to which this present teachings belong. Methods and materials similar or equivalent to those described herein can be used in the practice or testing of the present teachings. In case of conflict, the patent specification, including definitions, will control. In addition, the materials, methods, and examples are illustrative only and not intended to be limiting.

We claim:

1. A device configured to be positioned across an aperture in an atrial septum comprising,
 a distal portion comprising a distal end and a proximal end and having a first elongated configuration and a second radially expanded configuration, wherein the distal end has a size greater than the proximal end in the second radially expanded configuration;
 a proximal portion comprising a distal end and a proximal end and having a first elongated configuration and a second radially expanded configuration, wherein the proximal end has a size greater than the distal end in the second radially expanded configuration;
 a middle portion joining the distal end of the proximal portion at one end, and the proximal end of the distal portion at the other end;
 a first retrieval portion joining the proximal end of the proximal portion, wherein the first retrieval portion has a plurality of struts, and the retrieval portion has a first elongated configuration wherein the plurality of struts are straightened and kept close to one another and proximal to the elongated proximal portion, and a second radially expanded configuration wherein one end of at least one of the plurality of struts is positioned radially outwardly from the other end of the strut; and
 a second retrieval portion joining the distal end of the distal portion, wherein the second retrieval portion also has a plurality of struts.

2. The device of claim 1, wherein as the proximal, distal, middle and first and second retrieval portions are at their second radially expanded configuration, the device comprises an opening configured to allow blood to flow from a first end through the device to a second end.

3. The device of claim 1, wherein at least one of the distal and proximal portions is configured to have a cone shape in its second radially expanded configuration.

4. The device of claim 1, wherein the proximal portion of the device is larger than the distal portion of the device.

5. The device of claim 1, wherein in its second radially expanded configuration, the first retrieval portion is proximal to the proximal portion of the device.

6. The device of claim 1, wherein in its second radially expanded configuration, the first retrieval portion is within a general structural space of the radially expanded proximal portion.

7. The device of claim 1, wherein in its second radially expanded configuration, the second retrieval portion is within a general structural space of the radially expanded distal portion.

8. The device of claim 1, wherein the first retrieval portion further comprise a proximal hub configured to attach to a percutaneous delivery system.

9. A device configured to be positioned across an aperture in an atrial septum comprising,
 a plurality of lengthwise supports joining together with a plurality of perimeter supports, wherein at least one perimeter support joining a distal end of the plurality of lengthwise supports, at least one perimeter support joining a proximal end of the plurality of lengthwise supports, and at least one perimeter support joining the plurality of lengthwise supports at a place between the distal and proximal ends, a plurality of first retrieval struts, wherein a distal end of the first retrieval struts joins the proximal end of the lengthwise supports, a plurality of second retrieval struts, wherein a distal end of the second retrieval struts joins the distal end of the lengthwise supports, and wherein the lengthwise supports have a first generally straight configuration, and a second configuration wherein both ends of the lengthwise supports bend radially outwardly while at least one place between the two ends remain unchanged.

* * * * *